United States Patent [19]

Adler

[11] 4,027,623
[45] June 7, 1977

[54] SAMPLE MIXER AND SPREADER

[75] Inventor: Stanford L. Adler, Monsey, N.Y.

[73] Assignee: Technicon Instruments Corporation, Tarrytown, N.Y.

[22] Filed: June 23, 1975

[21] Appl. No.: 589,483

[52] U.S. Cl. ............................... 118/108; 118/120; 118/242; 118/257; 118/407

[51] Int. Cl.² .......................................... B05C 1/14

[58] Field of Search ............ 118/257, 57, 120, 108, 118/407, 401, 242; 427/2, 346, 434

[56] References Cited

UNITED STATES PATENTS

| | | | |
|---|---|---|---|
| 2,353,852 | 7/1944 | Rowland et al. | 118/242 X |
| 2,426,572 | 8/1947 | Alderfer | 118/413 |
| 3,442,196 | 5/1969 | Johnson | 118/257 X |
| 3,676,216 | 7/1972 | Abitboul | 118/57 X |

Primary Examiner—John P. McIntosh
Attorney, Agent, or Firm—S. P. Tedesco

[57] ABSTRACT

Apparatus for preparing a smear of a biological fluid substance containing cellular material on a first element having a surface for receiving the smear, utilizing a second element coacting with the first element. The elements are supported so that at least portions thereof are in close proximity to one another at a sample-applying station. A relatively small quantity of such biological liquid sample is introduced between the aforementioned element portions at the sample-applying station for spreading of the sample across at least the central portion of at least one of the aforementioned elements. The sample is spread or smeared on the aforementioned surface of the first element by moving one of the elements relatively to the other. The sample is mixed at least during the drawing of the sample so as to obtain a random distribution of such cellular material and enhance spreading such cellular material in a direction normal to the drawing of the sample.

7 Claims, 9 Drawing Figures

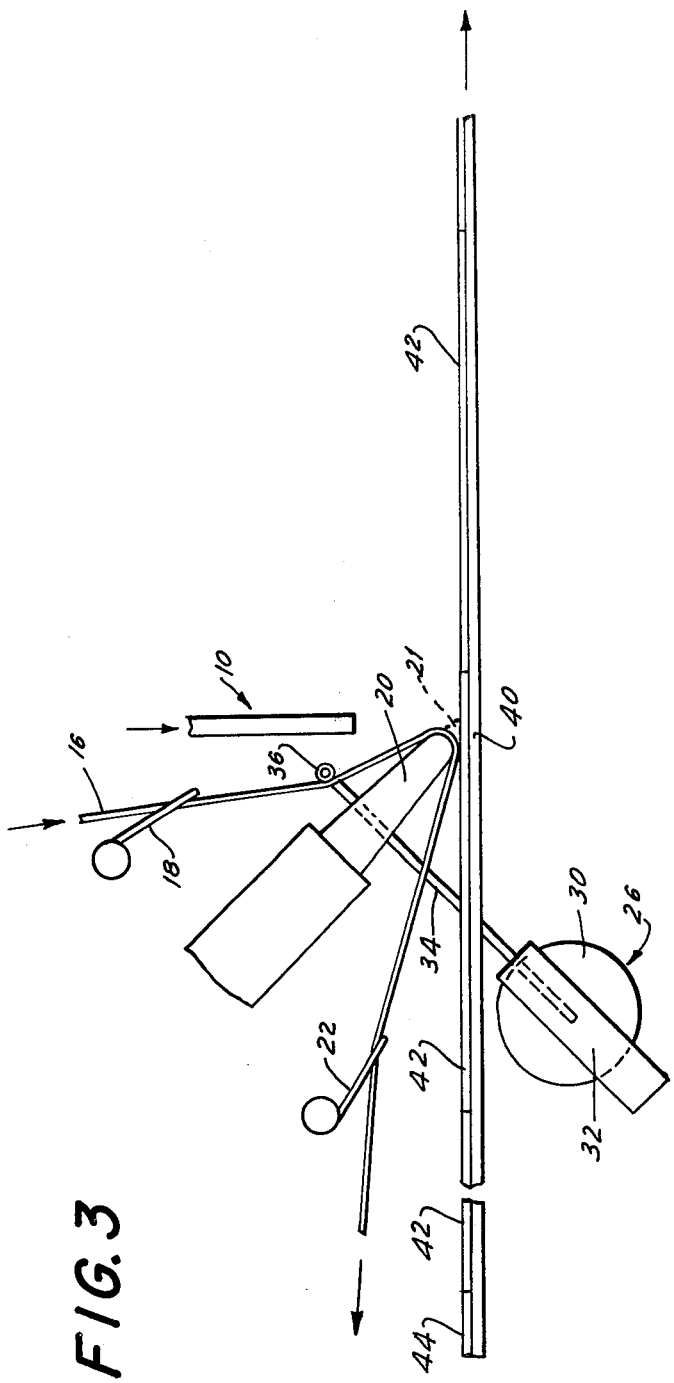
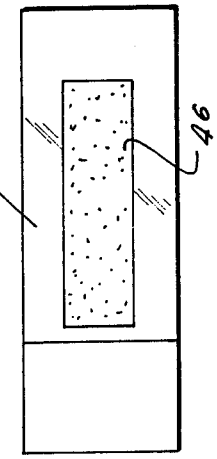
FIG. 3
FIG. 4

4,027,623

SAMPLE MIXER AND SPREADER

BACKGROUND OF THE INVENTION

1. Field of the Invention

This invention relates to the preparation of biological smears on substrates for microscopic examinations.

2. Prior Art

Heretofore, smears of biological substances such as blood or cellular suspensions have been prepared for microscopic examinations by manipulation of microscope slides and slide cover slips. The technique requires a certain degree of expertise and, even with such skill, resulting smears have tended to lack uniformity and reproducibility. In the common manual preparation technique in which an end edge of an elongated slide is drawn lengthwise along a glass strip or another such slide to smear a droplet of blood on the last-mentioned slide, the heavier cellular material tends very strongly to move out or away from the central portion of the smear to be left on the smear in congregations along the margins thereof. This is undesirable for microscopic examinations. For such examinations it is desirable in many instances that the cellular distribution be substantially even across the width of the smear throughout any given portion of the smear.

It has been proposed that smears be prepared by a spinning process, an apparatus for carrying out such process has been commercially available. The process is one of centrifuging on a microscope slide a volume of biological fluid such as blood for a period sufficient to spread the specimen over a portion of the slide. A drawback in such use of spinners is that an excess of liquid specimen such as blood is spun off the slide to spray the environment such as ambient air and also splatter the inner wall surface of the spinner. Such blood specimens may carry infectious diseases, and hence the required cleanup operation of such spinners after use may be hazardous.

It is desired to obviate the aforementioned problems in the preparation of smears of biological substances. Moreover, it is desired to provide a method and apparatus for preparation of such smears which may be readily automated.

SUMMARY OF THE INVENTION

One object of the invention is to provide an apparatus for preparing superior smears of biological fluids substances containing cellular material for microscopic examination. Another object is to provide apparatus for preparing smears of the quality characterized above which is readily automated. Still another object is to provide such technique and apparatus which has a further advantage that any excess biological specimen not adhering to the substrate for the smear may be easily confined and collected for simple disposal and greater safety for users of the apparatus. There is provided, in the technique for preparing a smear such as characterized on a first element having a surface for receiving the smear, utilizing a second element coacting with the first element, having the steps of supporting the elements so that at least portions thereof are in close proximity to one another at a sample-applying station, introducing a relatively small quantity of such biological liquid sample between the aforementioned element portions at the sample-applying station for spreading of the sample across at least the central portion of at least one of such elements, and drawing the sample on the aforementioned surface of the first element by moving one of such elements relatively to the other; the combination of mixing such sample at least during such drawing of the sample so as to obtain a uniform distribution of the cellular material, and enhance spreading of such cellular matter in a direction normal to the drawing of the sample.

BRIEF DESCRIPTION OF THE DRAWINGS

In the drawings:

FIG. 3 is a view similar to FIG. 1 but illustrating a modified form of the apparatus;

FIG. 4 is a top plan view of a microscope slide carrying on the upper surface thereof a smear made in accordance with the invention;

DETAILED DESCRIPTION OF THE PREFERRED EMBODIMENTS

Figure 1:
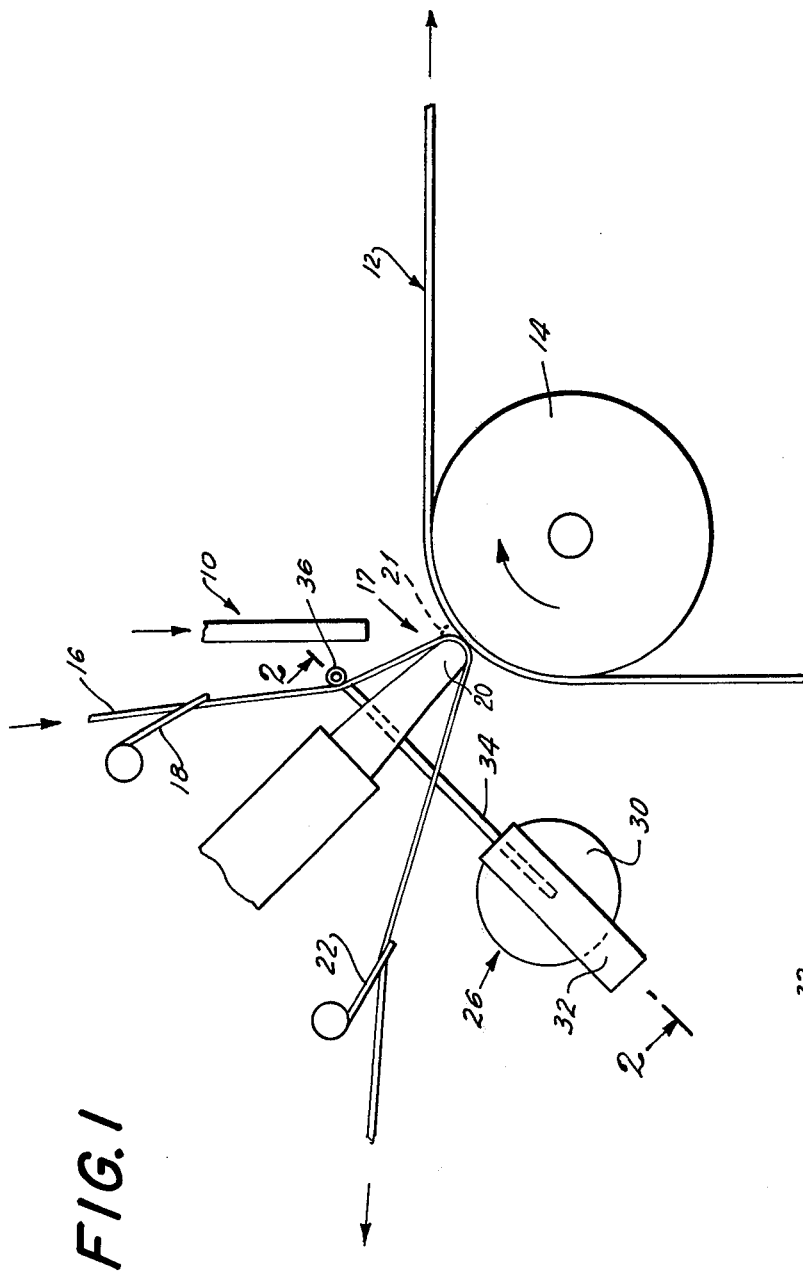
FIG. 1 is fragmentary, elevational view illustrating somewhat diagramatically apparatus embodying the invention.
Figure 2:
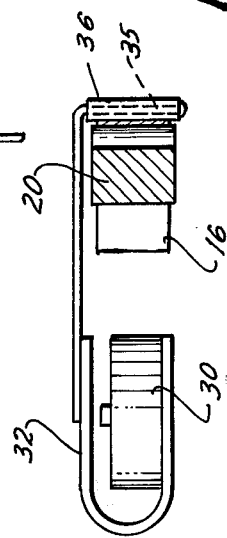
FIG. 2 is taken on line 2—2 of FIG. 1.

In FIG. 1, there is indicated at 10 a fixed dispensing probe for dispensing through the lower outlet end thereof sequentially at intervals, biological fluid samples containing cellular material which may be samples of whole blood or other biological fluids containing cellular material such as bacteria. The probe 10 may be of the type shown in my U.S. Pat. No. 3,871,895, and supplied by samples from a sampler such as shown in that patent. The disclosure of that patent is incorporated herein.

A strip of tape 12 is trained over a nontranslatory roller 14 and supplied from a nonillustrated source. It is advanced intermittently by nonillustrated pinch rollers. However, if desired, the roller 14 may be driven in the manner of a capstan with the tape being pressed against it by a nonillustrated idler. Cooperating with the tape 12 which is moved in the direction of the arrow, is a ribbon 16 fed from a nonillustrated source and advance periodically in nonillustrated manner as by pinch rollers in the direction of the arrow. The ribbon 16 extends over a fixed guide 18 which has guiding contact with the side edges of the ribbon as well as contact with one surface thereof. This ribbon 16 is trained over a stationary guide finger 20 at a sample-applying station 17 and the run of the ribbon 16 extends over a guide 22 similar to the guide 18. As shown in FIG. 1, the rounded (FIG. 1) distal end of finger 20 over which the ribbon 16 passes may guide the ribbon in such fashion that it contacts the tape 12 across a major portion thereof or is slightly spaced therefrom. Each sample is dispensed from probe 10 in the form of a droplet which falls into the cusp formed between the ribbon 16 and the tape 12 and forms a meniscus, as at 21.

A mixer, indicated generally at 26, is provided to mix the droplet of blood which is dispensed into the aforementioned cusp at the sample-applying station at least as early as the movement of the tape 12 to draw the sample thereon, such mixing having a significant affect on such dispensed sample to achieve a uniform distribution of lighter and heavier cells and enhance spreading of the sample in a direction normal to the drawing of the sample. The smear resulting from the drawing of the sample is in FIG. 5 of my U.S. Pat. No. 3,871,895. In the illustrated form the mixer comprises a buzzer coil 30 which is 60 cycle AC electromagnet having an armature in the form of a leaf spring 32, one end of which is supported in fixed position as is the electromagnet 30. The armature 32 has an extension 34 thereof of rodlike form fixed to the armature. One end portion of the extension 34 is fixed to the free end portion of the armature 32. At the distal end portion thereof, the rod extension 34 has a right-angle bend and a foot portion 35 extending in a direction at right-angles to the plane of the free end portion of the armature 32. A roller 36 is mounted for rotation on the foot portion 35 in axially fixed position. The roller 36 extends across the ribbon 16 in an otherwise free area of the ribbon 16 as shown in FIG. 1. As shown in this view, the roller deflects the ribbon 16 in this area by pressure thereagainst. In this form the ribbon 16 extends between the roller and the finger 20. The electromagnet is preferably energized periodically and when energized the roller 36 has a primary component of movement transversely of the direction of the run of the ribbon. The roller 36 vibrates the ribbon 16 in this manner which agitates the sample in contact with the ribbon 16. Utilizing the electromagnet supplied by alternating current at 60 cycles per second during the drawing of a smear which extends over a period of approximately 3 minutes, the direction of movement of the foot portion 34 is changed approximately 165 times during the drawing of the smear which may be approximately 2.75 inches long. The excursion of the ribbon, in the region of the roller 36, in the last-mentioned direction may total 1/16 inch. However, the excursion in the same direction where the ribbon 16 is in contact with the tape 12 may be as little as 0.005 inch if ribbon 16 is in frictional contact with the tape 12.

On the introduction of the sample in the aforementioned cusp at the sample-applying station, the tape 12 and the ribbon 16 are stationary. Subsequent to such introduction, the ribbon 16 is moved in the direction of the arrow to remove the excess of the sample thereon. The ribbon movement is terminated. After this, the tape 12 is moved in the direction of the arrow to draw the sample thereon in the form of a smear, the cellular material being uniformly distributed, both longitudinally and transversely, due to the mixing action taking place. Prior to such movement of the tape 12, spreading of the sample across the tape 12 throughout the central portion thereof is enhanced by the mixing action. The tape 12 movement is stopped, and at this time the mixer 26 is preferably deenergized to prevent the coil from becoming overheated. After advancement of the tape 12 is terminated, the ribbon 16 is advanced again and stopped to present a fresh surface portion thereof to the cusp at the sample-applying station and to collect a used portion of the ribbon 16 on a nonillustrated spool. Subsequent to termination of the last-mentioned movement of the ribbon 16, the tape 12 is advanced once again a short distance and stopped. Thereafter the cycle may be repeated for each sample. As previously indicated, the mixer 26 may be energized prior to the introduction of the next sample into the cusp formed between the tape 12 and the ribbon 16 and continue in such state until the sample has been drawn.

In the modified form of the apparatus shown in FIG. 3 like reference numerals denote like parts. In the last-mentioned form, the smears of biological fluid substances such as blood, for example, are drawn seriatim on respective microscope slides. There is provided a support in the nature of an elongated track 40 for the sliding therealong of a series of microscope slides 42 in end-to-end relation abutting one another. A pusher 44 advances the slides intermittently. As shown in FIG. 3, the ribbon 16 is in contact with one such slide 42 forming an angle therebetween into which a sample in the form of a droplet is dispensed from the probe 10. The sequence of operation of the apparatus of FIG. 3 is identical to that previously described with reference to the form of FIG. 1. The mixer 26 is energized not later than the introduction of such droplet between the ribbon 16 and the last-mentioned slide 42. Subsequent to such sample introduction, the ribbon 16 is advanced to remove the excess sample. The pusher 44 is then rendered operative and moved in the direction of the arrow to draw the sample on the last-mentioned slide 42. The movement of the pusher 44 is then terminated. The ribbon 16 is then advanced again to present a fresh surface portion and to advance a used portion of the ribbon 16 to the nonillustrated collection spool. Advancing movement of the ribbon is terminated. Upon termination of the last-mentioned movement, the pusher is activated again to push the next-following slide 42 into position to receive the next sample, thereby displacing the smeared slide from the station 17 for later non-illustrated collection. As previously indicated, the mixer 26 may be deenergized after the drawing of the sample on the previous slide. The smear on such preceding microscope slide 42 has random distribution of cellular material throughout the transverse dimension of the smear and longitudinally thereof as a result of the action of the mixer 26 on the sample to mix it and enhance spreading of the sample across the slide. Such a smear is indicated at 46 in FIG. 4.

Figure 5:
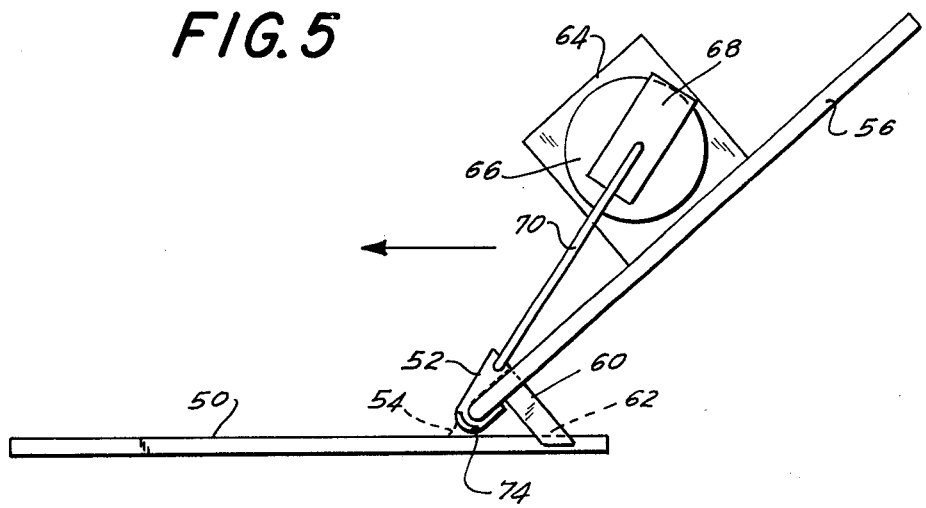
FIG. 5 is a side elevational view illustrating another modification of the invention.
Figure 6:
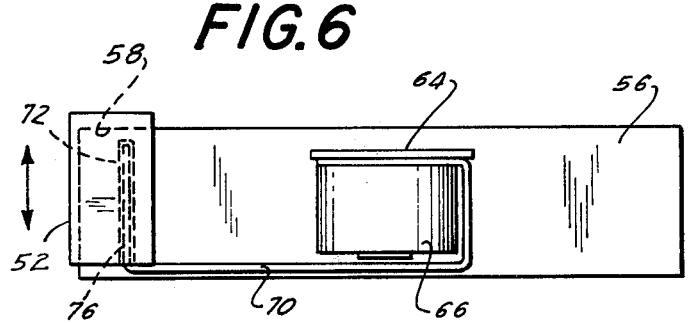
FIG. 6 is a top plan view of the apparatus of FIG. 5.
Figure 7:
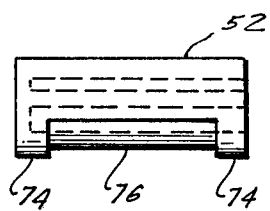
FIG. 7 is a front elevational detail view of an element of the apparatus of FIG. 5.
Figure 8:
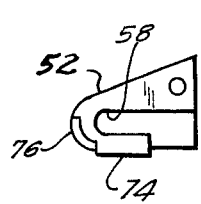
FIG. 8 is a side elevational detail view of such element.
Figure 9:
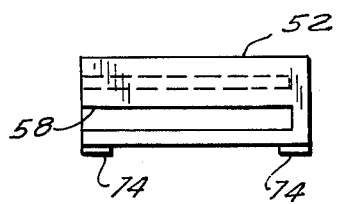
FIG. 9 is a rear elevational detail view of such element.

In the modified form of the invention illustrated in FIGS. 5 through 9, there is provided, for the preparation of a smear on a substrate element 50, an element 52 cooperating with the element 50 to draw a smear of a biological fluid sample containing cellular material upon the upper surface of the element 50 by movement of the element 52 from the position shown in FIG. 5 to the left along the upper surface of the element 50 which is illustrated as an elongated microscope slide. As shown in FIG. 5, a sample such as a droplet of blood is placed on the upper surface of the slide 50 and subsequent thereto the element 52, which extends transversely across the slide 50, is positioned such that the sample droplet forms a meniscus between the element 50 and the element 52, as at 54. In this manner, the sample is introduced between the elements 50 and 52. The element 52 is best shown in FIGS. 7–9.

The element 52 is supported from a generally oblong, planar support member 56 of relatively rigid material which may be of a suitable plastic for example. The support member 56 has at the front end thereof a rounded surface to be received within an elongated socket 58 best shown in FIGS. 6, 8 and 9. The last-mentioned surface of the member 56 extends to the bottom of the socket 58, and the construction is such that a portion of the socket overlaps the upper and under surfaces of the member 56 as well as one side edge thereof. The element 52, which may be formed of a suitable plastic material, is a disposable item as will appear hereinafter. The support member 56 has integrally formed therewith a pair of laterally spaced-apart legs, one being shown at 60, and each having in opposing relation to the other a shoulder 62. The legs 60 straddle the slide 50 in use so that each shoulder 62 coacts with the slide to support the support member 56 from the microscope slide 50 at the angle shown in FIG. 5 for example. The legs 60 contact only the lateral edge portions of the slide 50. Approximately midway between the ends of the support member 56, the latter has an upstanding flange 64 lying in a plane longitudinally of the member 56. Fixed to one face of the flange 64 is a 60 cycle AC electromagnet comprising a buzzer coil indicated at 66. Also fixed to the flange 64 is one leg of a generally U-shaped armature 68 in the form of a leaf spring.

In the manner of the form of FIG. 1, the armature 68 has a rod-like extension 70 in fixed relation thereto at one end. The distal end portion of the extension 70 is formed as a foot portion 76 extending at right angles to the other end portion of the extension 70. The last-mentioned foot portion is snugly received in a transverse bore 72 formed in the element 52, best shown in FIG. 6. In the manner of the form of FIG. 1, the movement of the foot portion 76 carries with it the element 52 on energization of the coil 66 during the drawing of the smear on the slide 50. The construction and arrangement is such that movement of the element 52 is largely transverse to the axes of the slide 50 and the support member 56, with the support element 52 having a total transverse excursion of approximately 1/16 inch when not engaged with the slide 50. When the element 52 is engaged with the slide 50, the total transverse excursion of the element 52 generated by the rod 70 may be 0.005 inch. This vibratory movement of the element 52 mixes the sample to uniformly distribute the lighter and heavier cellular material of the sample 54 and enhance transverse spreading of the sample as the slide 50 is moved relatively from the position of FIG. 5 toward the right while the coil 66 is energized. It may then be deenergized.

As best shown in FIG. 7, the element 52 has a pair of laterally spaced, downwardly extending projections 74 (typically 0.002 inch) which engage the upper surface of the slide 50 along its axial margins. The assembly of the element 52 with the support member 56 and the armature extension 70 is such that by manipulation of the armature extension 70 and the support element 52, the latter may be removed from the foot portion 76 for replacement by a fresh, unused support element 52. In the condition of FIG. 6, this disassembly is achieved by manipulation of the support element 52 in an upward direction relatively to the foot portion 76 and the member 56. Assembly of these elements is by manipulation thereof in the opposite direction, with the support element 52 sliding over the front end of the support member 56.

As shown in FIG. 7, the lower front, central portion of the element 52 has a shallow transverse recess therein which may be either textured to provide a somewhat rough finish or which receives in fixed relation, as by being cemented to the bottom of the recess, an insert 76 of a woven piece of fabric. The outer surface of such mesh material is provided for engagement with the biological sample 54. The mesh insert 76, like the ribbon 16 of the form of FIG. 1 which may also be of woven fabric, serves the function of entrapping the sample in such a manner that the sample is, in effect, metered from the mesh insert 78 during the drawing of the sample on the slide 50 by acting as a reservoir of such sample during such sample drawing. It serves the further function of retarding the lateral displacement of the heavier cellular material during the lateral or transverse spreading of the sample on the slide 50 to enhance random distribution of the cellular material in this direction.

In the use of the sample mixer and spreader of the form of FIG. 5, the sample is applied to a slide in the manner previously indicated, and then the slide 50 is suitably supported for relative movement with respect to the element 52 in the manner previously described. Such nonillustrated support of the slide may be provided by a friction table surface, not shown. Alternatively, the slide may be grasped, for example, between the thumb and forefingers of the left hand of the user, and the user's right hand may grip the support member 56 at the rear end portion thereof between the thumb and forefinger so as to push the element 52 along the slide 50 longitudinally thereof while the coil 66 is energized, thereby preparing the smear. The manner of support of the member 56 on the slide during this movement, as previously indicated, is through the engagement of the legs 60 of the member 56 with the slide and the engagement of the projections 74 of the element 52 with the slide.

While several forms of the sampler mixer and spreader have been illustrated, it will be apparent, especially to those versed in the art, that the sample mixer and spreader may take other forms and is susceptible of various changes in detail without departure from the principles of the invention.

What is claimed is:

1. Apparatus for preparing a smear of biological fluid sample containing particulates, comprising: an elongated first element movable along a first path and having a surface, said first element being movable at least in part a limited distance in a direction substantially transverse of said first path, an elongated second element having a surface movable along a second path, means locating portions of said surfaces longitudinally in at least close proximity to one another to define a cusp therebetween, means for selectively introducing a predetermined discrete volume of said sample between said surface portions, means for relatively moving said first and second elements along said first and second paths, respectively, to draw a smear of said sample on said second element surface, and means spaced from said locating means moving said first element back and forth in said transverse direction at least during relative movement of said first and second elements.

2. Apparatus as defined in claim 1, wherein: said means moving said first element in said transverse direction comprises a movable member extending at least in part transversely of said first element and engaging said first element.

3. Apparatus as defined in claim 1 wherein: said second element comprises a tape.

4. Apparatus as defined in claim 1 wherein: said first element comprises a flexible ribbon.

5. Apparatus as defined in claim 1 wherein: said second element comprises a rigid member.

6. Apparatus as defined in claim 1, wherein: said means moving said first element in said transverse direction comprises means generating a magnetic field.

7. A device for preparing a smear of biological fluid sample on an oblong substrate having a surface for receiving the smear, comprising: a relatively rigid oblong element having a handle portion at one end, said element including means remote from the other end of said element and adapted to engage the lateral edges of said substrate surface to support said element from said substrate at a predetermined angle thereto, a member supported at said other end of said element and adapted to contact at least a portion of the width of said substrate surface, said member being slideably mounted on said other end of said element, and means supported on said element driving said member back and forth transversely of said element.

* * * * *